United States Patent
Blank

(10) Patent No.: US 10,322,017 B2
(45) Date of Patent: Jun. 18, 2019

(54) MEDICAL IMPLANT SUCH AS A STENT

(71) Applicant: Angiomed GmbH & Co. Medizintechnik KG

(72) Inventor: Thiemo Blank, Plankstadt (DE)

(73) Assignee: Angiomed GmbH & Co. Medizintechnik KG, Karlsruhe (DE)

( * ) Notice: Subject to any disclaimer, the term of this patent is extended or adjusted under 35 U.S.C. 154(b) by 210 days.

(21) Appl. No.: 15/400,909

(22) Filed: Jan. 6, 2017

(65) Prior Publication Data

US 2017/0112644 A1 Apr. 27, 2017

Related U.S. Application Data

(62) Division of application No. 11/572,681, filed as application No. PCT/EP2005/008324 on Aug. 1, 2005, now abandoned.

(30) Foreign Application Priority Data

Jul. 30, 2004 (GB) .................................. 0417077.5

(51) Int. Cl.
*A61F 2/91* (2013.01)
*B23K 15/08* (2006.01)
(Continued)

(52) U.S. Cl.
CPC ................ *A61F 2/91* (2013.01); *B23K 15/08* (2013.01); *B23K 26/38* (2013.01); *B26F 3/004* (2013.01);
(Continued)

(58) Field of Classification Search
CPC ...... A61F 2230/0006; A61F 2230/0069; A61F 2240/001; A61F 2/91; B23K 15/08; B23K 2101/06; B23K 26/38; B26F 3/004
See application file for complete search history.

(56) References Cited

U.S. PATENT DOCUMENTS 6,036,708 A 3/2000 Sciver
6,102,943 A 8/2000 McGuinness
(Continued)

FOREIGN PATENT DOCUMENTS

| GB | 2369062 A | 5/2002 |
| WO | 2001030271 A2 | 5/2001 |
| WO | 2003000157 A1 | 1/2003 |

OTHER PUBLICATIONS

CA 2,575,364 filed Jan. 26, 2007 Examiner's Requisition dated Feb. 13, 2012.
(Continued)

*Primary Examiner* — Stephen Choi
(74) *Attorney, Agent, or Firm* — Rutan & Tucker, LLP

(57) ABSTRACT

A medical implant such as a self-expanding shape memory alloy stent with a strut matrix formed by cut patterns in a wall of a tubular workpiece can be enhanced by arranging for the line of the laser beam when cutting the struts to be one that does not pass through the longitudinal rotational axis of the tubular workpiece. Such "off-axis" cutting can modify the cross-sectional shape and area of each strut, along its length. Such modulation can enhance the fatigue resistance of the stent matrix, or increase the radial force that the stent matrix is capable of exerting on bodily tissue within which it is implanted.

11 Claims, 1 Drawing Sheet

(51) Int. Cl.
*B26F 3/00* (2006.01)
*B23K 26/38* (2014.01)
*B23K 101/06* (2006.01)

(52) U.S. Cl.
CPC ............... *A61F 2230/0006* (2013.01); *A61F 2230/0069* (2013.01); *A61F 2240/001* (2013.01); *B23K 2101/06* (2018.08)

(56) References Cited

U.S. PATENT DOCUMENTS

| | | | |
|---|---|---|---|
| 6,162,245 A | 12/2000 | Jayaraman | |
| 6,409,753 B1* | 6/2002 | Brown | A61F 2/90 623/1.15 |
| 6,475,233 B2* | 11/2002 | Trozera | A61F 2/91 623/1.14 |
| 6,488,702 B1 | 12/2002 | Besselink | |
| 6,592,616 B1 | 7/2003 | Stack et al. | |
| 7,789,906 B2 | 9/2010 | Blank | |
| 2002/0038146 A1* | 3/2002 | Harry | A61F 2/91 623/1.16 |
| 2002/0193824 A1* | 12/2002 | Boylan | A61F 2/013 606/200 |
| 2002/0198589 A1* | 12/2002 | Leong | A61F 2/91 623/1.15 |
| 2003/0014101 A1* | 1/2003 | Harrison | A61F 2/91 623/1.15 |
| 2003/0045923 A1* | 3/2003 | Bashiri | A61F 2/91 623/1.12 |
| 2004/0064179 A1* | 4/2004 | Linder | A61F 2/013 623/1.11 |

OTHER PUBLICATIONS

GB 0417077.5 filed Jul. 30, 2004 Search Report dated Oct. 27, 2004.
PCT/EP2005/008324 filed Aug. 1, 2005 International Preliminary Report on Patentability dated Jan. 30, 2007.
PCT/EP2005/008324 filed Aug. 1, 2005 Search Report dated Oct. 14, 2005.
PCT/EP2005/008324 filed Aug. 1, 2005 Written Opinion dated Oct. 14, 2005.
U.S. Appl. No. 11/572,681, filed Jan. 23, 2008 Non-Final Office Action dated Oct. 4, 2013.
U.S. Appl. No. 11/572,681, filed Jan. 23, 2008 Advisory Action dated Aug. 11, 2014.
U.S. Appl. No. 11/572,681, filed Jan. 23, 2008 Advisory Action dated Jun. 28, 2011.
U.S. Appl. No. 11/572,681, filed Jan. 23, 2008 Final Office Action dated Apr. 14, 2011.
U.S. Appl. No. 11/572,681, filed Jan. 23, 2008 Final Office Action dated Jun. 18, 2012.
U.S. Appl. No. 11/572,681, filed Jan. 23, 2008 Final Office Action dated Jun. 2, 2014.
U.S. Appl. No. 11/572,681, filed Jan. 23, 2008 Final Office Action dated Mar. 30, 2010.
U.S. Appl. No. 11/572,681, filed Jan. 23, 2008 Non-Final Office Action dated Dec. 23, 2011.
U.S. Appl. No. 11/572,681, filed Jan. 23, 2008 Non-Final Office Action dated Oct. 8, 2010.
U.S. Appl. No. 11/572,681, filed Jan. 23, 2008 Non-Final Office Action dated Sep. 28, 2009.

* cited by examiner

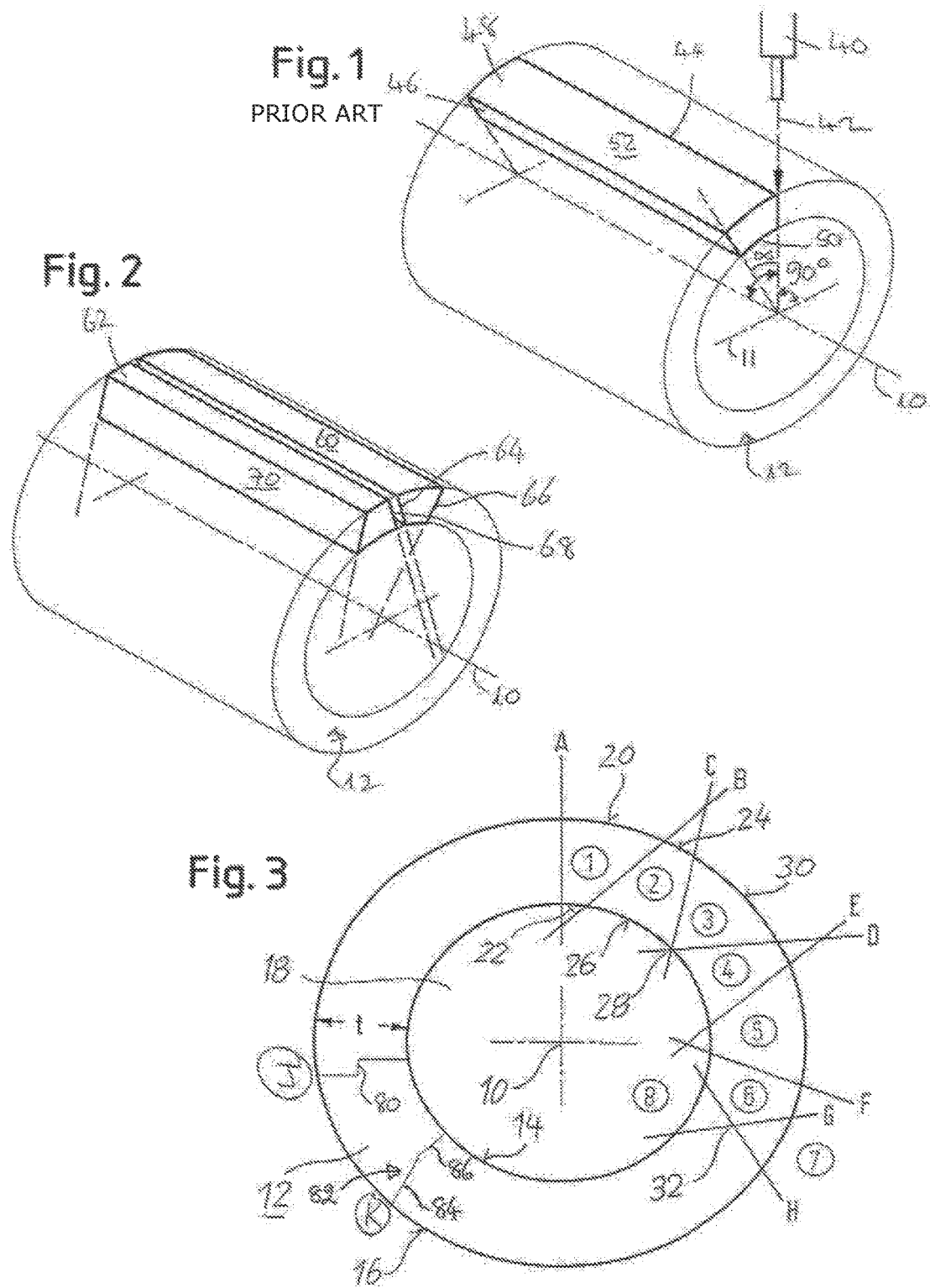

MEDICAL IMPLANT SUCH AS A STENT

PRIORITY

This application is a divisional application of U.S. application Ser. No. 11/572,681, filed on Jan. 23, 2008, which is a National Stage entry under 35 U.S.C. 371 of PCT/EP2005/008324, filed on Aug. 1, 2005, which claims priority to UK Patent Application No. 0417077.5, filed on Jul. 30, 2004, the entireties of which are hereby incorporated by reference.

FIELD OF TECHNOLOGY

This invention relates to a medical implant (such as a stent) with a matrix of elongate struts arranged about a central longitudinal axis (long axis), the struts being joined at nodes, each said strut having a thickness between a luminal surface and an abluminal surface, and opposed lengthwise flank surfaces, one each side of the strut.

SUMMARY OF THE INVENTION

Generally, stents fall into two classes, namely, balloon-expandable stents and self-expanding stents. Typically, a balloon-expandable stent is made of stainless steel, from a stainless steel tube, by laser cutting, or perhaps by chemical etching. In one class of self-expanding stents, raw tube stock of nickel-titanium shape memory alloy is cut with a laser, to form a matrix of struts, and then the so-cut stent precursor is heat treated to provide it with a "memory" of a radially expanded disposition. The stainless steel balloon expandable stent is loaded onto a cylindrical balloon for delivery to a stenting site, and is then deployed by inflation of the balloon to cause plastic deformation of the nodes and struts of the matrix. Typically, a self-expanding nickel-titanium shape memory shape alloy stent is compressed into a confining cylindrical sheath, and deployed at the stenting site by proximal withdrawal of the sheath, progressively to release the stent, starting at its distal end.

Fatigue performance of the metal of the struts and nodes can be important, for example when the stent is flexed by a pressure pulse corresponding to each beat of the heart of the patient in which the stent is installed. In any event, the ability of the stent to flex during delivery on a catheter through a tortuous bodily lumen, and the ability of the stent to maintain patent the lumen in which it is deployed, puts severe demands on the mechanical properties of the nodes, and the struts.

Many stents are formed from tube stock by laser cutting the tube to form the strut matrix that characterizes the stent. Typically, the cutting beam of the laser is directed vertically downwardly, towards a table, and the workpiece is mounted on the table, beneath the beam, for rotation about its longitudinal axis relative to the beam, and for axial movement perpendicular to the beam and perpendicular to the longitudinal axis, but with the beam in all cutting dispositions of the stent being arranged on a line which passes through the central longitudinal axis of the stent, that is to say, the longitudinal axis at the center of the tube stock. This in consequence results in struts that have one opposed pair of arcuate luminal (radially inside) and abluminal (radially outside) surfaces, and one opposed pair of flank surfaces, cut with the laser, with a line of action that can be projected through the central longitudinal axis of the stent. See FIG. 1 of the accompanying drawings.

Although the above description describes cutting with a laser it will be apparent that other cutting techniques are possible, such as by jets of energy (electron beam for example) or jets of fluid (water for example) as well as other cutting techniques such as chemical or electrical etching techniques. Whereas the advantages of the invention are evident most readily in metal stents, they are also available in implants other than stents (filters, for example) and materials other than metal (shape memory polymers, for example).

The basic function of a stent is to urge bodily tissue radially outwardly from the stented lumen, and prevent its ingress into the lumen. Stent performance therefore varies with the radial strength of the stent matrix, and thus in general with the pattern of the stent matrix and in particular with the fineness of the stent mesh. It is an object of the present invention to manage these parameters more effectively. A further object is to refine the fatigue resistance (or load-bearing potential) of the stent by improvements in the design of the stent matrix.

These technical effects can be achieved by the technical features that characterize the present invention, namely:
1. the flank surfaces of the struts are formed by a jet cutter; and
2. at least a portion of at least one of the flank surfaces has a plane that does not intercept said rotational axis. We call this "off-axis" cutting.

As will be brought out more clearly below, with reference to the drawing, off-axis cutting opens up possibilities to achieve, for any given number of struts around a circumference of the stent, a higher radial strength, or smaller apertures in the stent matrix.

Incidental benefits could include the provision of sharp edges to the struts that would allow, for example, a cutting function of such a strut. One could modulate strut width along the length of each strut. By modulating the cross-sectional dimensions of the strut, along the length of the strut, one can compensate for varying levels of stress suffered by the material within each strut, so that stress levels vary less, within the strut matrix, from one location to another. A consequence is that fatigue performance can be enhanced, by removal of the peaks of stress that would otherwise place a limit on the fatigue performance.

Conventionally, the line of action of the laser or jet beam cutter that cuts the stent matrix from a tubular workpiece is perpendicular to the long axis of the workpiece, as well as passing through the long axis. A practical reason for this conventional practice is that the workpiece is more or less one dimensional, being long, but with a small cross-section, so it is easy to rotate under the laser cutting beam around its long axis, and relatively easy to translate (as with a microscope stage) so as to deliver an axial length to an "off-axis" cut surface. It is not so easy, however, to arrange to tilt or turn the workpiece length relative to the laser beam. It is within the scope of the present invention, nevertheless, to orient the line of action of the beam and the line of the said long axis at varying angles, or at an angle other than 90°. Either the laser is mounted for tilting or turning movement relative to the workpiece, or the workpiece is so mounted in a jig that its length can be tilted or turned relative to the line of action of the laser cutting beam. By presenting the beam not perpendicular to the long axis of the workpiece, flank surfaces can be created that further refine the mechanical performance of the implant, relative to the performance of implants with conventionally cut struts.

BRIEF DESCRIPTION OF THE DRAWINGS

For a better understanding of the present invention, and to show more clearly how the same may be carried into effect, reference will now be made to the accompanying drawings, in which:

FIG. 1 is an isometric view of a jet cutter cutting an annular workpiece;

FIG. 2 is an isometric view of a workpiece as in claim 1, which exhibits three cut surfaces created by the jet cutter; and FIG. 3 is a transverse section through the workpiece, showing cut lines A to K.

DETAILED DESCRIPTION

In FIG. 1, tube stock has a long axis 10 and a jet cutter 40, which is a laser, creates a cutting beam 42 which lies on a line that intersects the axis 10. A cut surface 44 is created, which is planar, the plane including the long axis 10. As shown in FIG. 1, the laser beam 42 is perpendicular to the long axis 10 and is also perpendicular to the short axis (radial axis) 11.

By rotating the workpiece around its long axis 10, through an angle a, and then activating again the laser 40, then translating the workpiece along its long axis, one can make a second cut surface 46 which is also planar and also intersects the long axis 10, but which is not parallel to the cut surface 44. Between the two cut surfaces 44, 46, lies a segment of the workpiece with an arcuate abluminal surface 48 and an arcuate luminal surface 50. The cut surfaces 44, 46 are to be regarded as the flank surfaces of an element 52 of an incipient strut matrix to be created out of the tube stock 12 by the laser 40.

Such a cutting operation to create a stent matrix is conventional. Conventionally, the matrix is created out of tube stock that has a diameter corresponding to a small diameter delivery configuration of the stent, with small gaps between struts of the matrix that correspond to the width of the laser beam. However, it has been proposed to create the strut matrix at a diameter more nearly corresponding to the deployed diameter of the stent after placement at a stenting site, the thus-created matrix being crimped or otherwise reduced in diameter when the stent is to be transluminally delivered and deployed. Using a larger diameter than the small diameter delivery configuration has the advantage that for a given manufacturing tolerance a wider range of off-axis cutting is possible. Consequently, the present invention also includes creation of the stent strut matrices at this larger diameter, for example, from tube stock having a diameter more or less corresponding to the diameter of the stent after deployment.

Turning now to FIG. 2, we see two matrix struts 60, 62, also created by jet cutting from the same workpiece 12. Strut 60 has flank surfaces 64, 66 and strut 62 has flank surfaces 68, 70. All four flank surfaces are planar but none includes the long axis 10 because the beam 42 of the laser 40 does not intersect the axis 10 when forming the flank surfaces.

All flank surfaces 44, 46, 64, 66, 68, and 70 are planar, but need not be. For example, while the workpiece is being translated under the beam 42 in the direction of the axis 10, it could also simultaneously be rotated about its axis 10 or translated in a direction perpendicular to the line of axis 10.

Furthermore, the workpiece could be tilted and/or turned relative to the beam 42, so that the axis 10 is not at all times perpendicular to the line of the beam 42. The beam could even be coaxial with the long axis 10. With microprocessor control of the movement of the workpiece relative to the line 42 of action of the jet cutter, a range of desired strut sections and shapes is achievable. For example, using finite element analysis, FEA, to design a strut matrix with a more uniform stress distribution throughout the strut matrix can lead to specifications for strut configurations that are more complex than shown in FIGS. 1 and 2. Judicious programming of a jet cuter worktable can permit a realisation of strut shapes approximating to the configurations calculated by the FEA.

FIG. 3 shows a schematic section through a stent perpendicular to the rotational long axis 10 of tube stock 12. The tube stock has a luminal surface 14 and an abluminal surface 16, with a lumen 18 and a wall thickness t measured in a diameter of the tube, between the luminal surface 14 and the abluminal surface 16.

Successive cuts A to H of the laser beam are shown as lines of action in the drawing, and the resultant strut cross-sections 1 to 8, between successive laser cuts, are indicated on the drawing. Specifically, strut 1 has flank surfaces defined by cuts A and B, and a relatively extensive abluminal surface area 20 but a rather small luminal surface area 22. By contrast, adjacent strut 2 has flank surfaces B and C, a relatively small abluminal area 24 and a correspondingly large luminal surface area 26. The next strut, strut 3, has only a line 28 of junction between its flank surfaces C and D defining its luminal surface, but a large surface area 30 of abluminal surface. Strut 4, with flanks D and E, resembles strut 2, and strut 5, with flanks E and F, resembles strut 1. Strut 6, with flank surface F, also has a flank surface which exhibits two flank portions G and H which meet at an edge 32. Struts 7 and 8, each with flank surfaces formed by cuts G and H, and a mere line 32 forming the luminal and abluminal surface, respectively, have thickness less than that of the wall of the tubular workplace, which may have utility in special applications. If such a thin strut is needed, then the unwanted material of the complementary strut (7 or 8) could be removed.

With conventional on-axis cutting, any two facing flank surfaces are spaced from one another already by the width of the laser beam that formed these cut surfaces and which intersects the long axis of the workpiece. Thus bodily tissue outside the implant can "see" the long axis inside the implant matrix along the line in which the beam was working. However, with off-axis cutting, one facing flank surface in a sense "over-lies" the other flank surface with respect to a line of sight along any radius to the long axis, and so prevents outside tissue "seeing" the long axis (unless the implant is radially so much expanded, that the facing strut flank surfaces have already moved circumferentially well away from each other).

Thus, for a given number of struts around the implant circumference, and a given amount of radial expansion, off-axis cutting offers the chance of smaller gap widths between adjacent struts in the expanded implant than with conventional on-axis cutting.

With conventional strut cross-sections emerging from "on-axis" cut surfaces, important for the mechanical strength of each strut is the maximum dimension in the section transverse to the strut length. Now, with off-axis cutting, one can provide a bigger dimension in each strut cross-section than with conventional on-axis cutting. For example, considering struts 1, 2 and 3 in the drawing, struts 1 and 3 have a larger dimension than an on-axis strut on their abluminal surface but strut 2 is not disadvantaged because it has a larger dimension on the luminal surface than would be its abluminal dimension in a conventional arrangement cut wholly on-axis. The area of the annulus of the workpiece is the same, and cut into the same number of strut sections, but each such section has one arcuate surface bigger than it would be with on-axis cutting, and the other smaller. The strength-giving effect of the bigger arcuate surface outweighs the loss of strength coming from the smaller arcuate surface.

It will be appreciated that continuation of the pattern of cutting, beyond cut-line H, around the remainder of the circumference of the tube 12, clockwise around to initial cut A, delivers around the full circumference of the tube the useful technical effect of providing each strut with strut width somewhat greater than is the case with the conventional "on-axis" line of action of the laser cutting beam. Thus, technical effects of off-axis cutting as described above are not confined to an enhancement of the surface area available for holding back tissue from the stented lumen. The mechanical performance of each strut depends significantly on the maximum dimension of the strut around the circumference of the stent envelope. With off-axis cutting, one can provide each strut with a greater dimension in the circumferential direction of the envelope than would be the case with the prior art on-axis cutting.

In this way, even though the raw tube stock material is unchanged, and the number of struts per circumference is unchanged, nevertheless the stent matrix produced by off-axis cutting is stronger because it exhibits a i) bigger apparent surface area of struts to put back the bodily tissue from the lumen (or smaller gap widths), and ii) provides each of the struts with greater strength to push back the tissue.

In the simplest case, the orientation of each cut-line with respect to the workpiece does not vary as the workpiece is advanced axially while the laser cuts along the length of each strut. However, in more sophisticated designs, there can be manipulation of the workpiece as the laser advances along the length of each strut. One reason to perform such manipulation is to co-ordinate the cross-sectional area of each strut with the distance away that portion of the strut is from a bending node of the stent strut matrix between adjacent struts. Such co-ordination allows management of stress patterns within each strut, thereby to eliminate zones where stress is higher than elsewhere, thereby to render stress much more uniform throughout the strength strut matrix, thereby to improve the fatigue performance of the stent in general.

It will be appreciated that the contribution which this invention makes to the art is not limited to cutting by laser but is applicable to any cutting technology, for example which involves a beam of energy, a beam of particles, or a jet of fluid, whether gas or liquid.

Further, it will be appreciated that the contribution which this invention makes to the state of the art is not confined to metal stents but is applicable to other devices, for example, stent grafts, filters for temporary placement within a bodily lumen, or even devices which are not medical and not for placement in bodily lumens.

Reverting to FIG. 3, attention is now drawn to cut lines J and K. These are cut lines that include a discontinuity (which cut lines A to H do not exhibit). A discontinuity may be advantageous in a number of ways. For example, a discontinuity can inhibit or substantially prevent relative radial movement of the struts facing one another across the cut line (at least while the stent is in a radially small intraluminal delivery configuration). Further, should any such movement occur, the discontinuity could serve to bring back to a desired compact annular starting configuration the relative positions of the facing struts.

Cut line J features a step 80 at a location within the wall thickness t of the workpiece annulus 12. Such a step can be imparted to an initially planar cut line by, for example, mechanical stamping, chemical etching and deposition or spark deposition and erosion, while there is spacing between the facing cut surfaces at the cut line J.

Likewise, the change of gradient along the line 82 in cut line K, where two planar portions 84, 86 of the cut line intersect, can also be created by techniques such as those named in the paragraph above. Other techniques will be known to those skilled in the art of micro-machining of small metal workpieces.

What is claimed is:

1. A method of forming a medical implant from a tubular workpiece, the tubular workpiece having a longitudinal axis and a wall defining a lumen along the longitudinal axis, the method comprising
    positioning the tubular workpiece in a jet cutting apparatus;
    forming a plurality of struts in the tubular workpiece with a beam of the jet cutting apparatus, comprising:
        cutting a first portion of the wall along a first line from an abluminal surface of the tubular workpiece to a first line end point, wherein the first line does not intersect the longitudinal axis;
        translating the tubular workpiece relative to the beam; and
        cutting a second portion of the wall along a second line from the first line end point to a luminal surface of the tubular workpiece, wherein the second line forms a non-zero angle with the first line.

2. The method of claim 1, wherein the first line and the second line together create a multifaceted first flank of a first strut.

3. The method of claim 2, wherein the forming step further comprises cutting a second flank of the first strut in the wall adjacent the first flank, the second flank extending from the abluminal surface to the luminal surface of the tubular workpiece.

4. The method of claim 3, wherein the second flank is multifaceted.

5. The method of claim 3, wherein the first flank and the second flank together create a sharp cutting edge.

6. The method of claim 3, wherein the first strut has a luminal surface area smaller than an abluminal surface area.

7. The method of claim 6, wherein the forming step further comprises cutting a third flank in the wall adjacent the second flank, the second flank and the third flank defining sides of a second strut, wherein the second strut has a luminal surface area larger than an abluminal surface area.

8. The method of claim 1, wherein the medical implant is a stent designed for intraluminal positioning in a patient.

9. The method of claim 1, wherein the beam of the jet cutting apparatus is an electron beam.

10. The method of claim 1, wherein the beam of the jet cutting apparatus is a jet of fluid.

11. The method of claim 1, wherein the beam of the jet cutting apparatus is a laser beam.

* * * * *